(12) United States Patent
Lin et al.

(10) Patent No.: US 11,828,754 B2
(45) Date of Patent: Nov. 28, 2023

(54) MODIFIED ELECTRODE, MANUFACTURING METHOD THEREOF AND USE THEREOF

(71) Applicant: NATIONAL CHENG KUNG UNIVERSITY, Tainan (TW)

(72) Inventors: Chia-yu Lin, Tainan (TW); Shu-yu Lin, Tainan (TW); Yi-hsuan Lai, Tainan (TW); Shih-ching Huang, Tainan (TW); Tzu-hsuan Wang, Tainan (TW); Ting-rong Ko, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 0 days.

(21) Appl. No.: 17/820,879

(22) Filed: Aug. 18, 2022

(65) Prior Publication Data
US 2023/0314423 A1    Oct. 5, 2023

(30) Foreign Application Priority Data
Mar. 31, 2022   (TW) .................................. 111112697

(51) Int. Cl.
*G01N 33/543*    (2006.01)
*G01N 33/68*    (2006.01)

(52) U.S. Cl.
CPC ..... *G01N 33/5438* (2013.01); *G01N 33/6827* (2013.01)

(58) Field of Classification Search
None
See application file for complete search history.

(56) References Cited

FOREIGN PATENT DOCUMENTS

CN    111487302 A    8/2020

OTHER PUBLICATIONS

Nazaruk et al. (Anal Bioanal Chem '2010' 398:1651-1660) (Year: 2010).*
Luo et al. (Chemical Engineering Journal 165 '2010' 524-528) (Year: 2010).*
Yi-Kai Chih, Ming-Chang Yang, "An 2,2'-azino-bis (3-ethylbenzthiazoline-6-sulfonic acid)-immobilized electrode for the simultaneous detection of dopamine and uric acid in the presence of ascorbic acid", Bioelectrochemistry, vol. 91, Jan. 23, 2013, p. 41-51.
Taiwanese Office Action issued in corresponding Taiwan Patent Application No. 111112697 dated Apr. 26, 2023, pp. 1-4.
Office Action issued in corresponding Taiwan Patent Application No. 111112697 dated Dec. 23, 2022, pp. 1-5.

* cited by examiner

*Primary Examiner* — Wojciech Haske
(74) *Attorney, Agent, or Firm* — PV IP PC; Wei Te Chung; Zhigang Ma

(57) ABSTRACT

A modified electrode, manufacturing method thereof and use thereof are provided. The manufacturing method includes steps of: mixing a carbon nanomaterial with 2,2'-azino-bis (3-ethylbenzthiazoline-6-sulfonic acid), followed by drop-casting on a screen-printed carbon electrode, to obtain carbon material modified electrodes; and electrochemically pre-treating the carbon material modified electrodes by cyclic voltammetry technique, constant potential technique, or constant current technique to obtain a modified electrode. 3-Ethyl-6-sulfonate benzothiazolinone imine and 3-ethyl-6-sulfonate benzothiazolone compound are formed on a surface of the modified electrode, and the modified electrode is used for protein analysis, protein immobilization and related biosensor, electrochemical catalysis or biofuel cells.

8 Claims, 11 Drawing Sheets
(3 of 11 Drawing Sheet(s) Filed in Color)

MODIFIED ELECTRODE, MANUFACTURING METHOD THEREOF AND USE THEREOF

CROSS REFERENCE TO RELATED APPLICATIONS

This application claims the priority of Taiwan Patent Application No. 111112697, filed on Mar. 31, 2022, titled "MODIFIED ELECTRODE, MANUFACTURING METHOD THEREOF AND USE THEREOF", and the disclosure of which is incorporated herein by reference. The patent or application file contains at least one drawing executed in color. Copies of this patent or patent application publication with color drawing(s) will be provided by the Office upon request and payment of the necessary fee.

FIELD OF INVENTION

The present disclosure relates to the technical field of an electrode, and particularly to a modified electrode. The present disclosure also relates to a manufacturing method, especially a method for manufacturing the modified electrode. The present disclosure also relates to a use, especially a use of the modified electrode.

BACKGROUND OF INVENTION

Chronic kidney disease is one of the top ten causes of death in Taiwan. Currently, radioimmunoassay, immunoturbidimetry, enzyme-linked immunosorbent assay, chemiluminescence immunoassay, and fluorescence immunoassay are used in medical treatment to detect albumin in urine for assessing whether kidney disease occurs. However, radioimmunoassay has the disadvantage of overestimating the concentration of albumin; immunoturbidimetry has the disadvantage of using a large number of antibodies; enzyme-linked immunosorbent assay and chemiluminescence immunoassay have high sensitivity, but the reagents used in enzyme-linked immunosorbent assay is harmful to the environment, and the reagents used in chemiluminescence immunoassays are very expensive.

In addition, the conventional technology also utilizes liquid chromatography-mass spectrometry (LC-M) and high-performance liquid chromatography (HPLC) to detect albumin in urine. The LC-MS and HPLC have high sensitivity, but they require complex and time-consuming sample preparation as well as sophisticated instrumentation, and is therefore unsuitable for generalized use.

Therefore, it is an urgent problem to be solved in the art of developing a sensor that is portable, highly sensitive, simple to be manufactured, and easy to be operated.

SUMMARY OF INVENTION

In order to solve the technical problems in the prior art described above, one object of the present disclosure is to provide a method of manufacturing a modified electrode. The object of rapidly manufacturing the modified electrode may be achieved by electrochemical pretreatment of an electrode.

Another object of the present disclosure is to provide a modified electrode. The object of enhancing the protein adsorption capacity may be achieved by 3-ethyl-6-sulfonate benzothiazolinone imine and 3-ethyl-6-sulfonate benzothiazolone compound present on the modified electrode.

Yet another object of the present disclosure is to provide a use of a modified electrode. The object of using the modified electrode for protein biosensors, such as urine albumin, or biofuel cells.

In order to achieve the objects described above, the present disclosure provides a method of manufacturing a modified electrode. The method comprises steps of:

mixing carbon nanomaterials with 2,2'-azino-bis(3-ethylbenzothiazoline-6-sulfonic acid) diammonium salt to form an electrode slurry, and drop-casting the electrode slurry on a screen-printed carbon electrode to obtain carbon material modified electrodes; and placing the carbon material modified electrodes in a phosphate buffer solution (PBS) or a sulfuric acid solution, and performing an electrochemical pretreatment by cyclic voltammetry method, constant potential method or constant current density method to obtain electrochemically-pretreated electrodes;

wherein the cyclic voltammetry method is performed by cycling at a scan rate of 100 mV/s to 500 mV/s between 0 V and 1.4 V vs. Ag/AgCl for 75 to 225 cycles, the constant potential method is performed by applying a potential of between 1.0 V and 1.2 V vs. Ag/AgCl for 1800 seconds, and the constant current density method is performed by applying a current density of between 0.5 mA cm$^{-2}$ and 5.0 mA cm$^{-2}$ until a charge passage of 46.0 mC cm$^{-2}$ is reached.

In one embodiment, after the electrochemical pretreatment, the method further comprises a step of rinsing the electrochemically-pretreated electrodes with PBS.

In one embodiment, the carbon nanomaterials comprise carbon nanotubes, graphene, graphene oxide, and reduced graphene oxide.

In one embodiment, a weight ratio of the carbon nanomaterials to the 2,2'-azino-bis(3-ethylbenzothiazoline-6-sulfonic acid) diammonium salt is between 1:4 and 2:1.

In one embodiment, the weight ratio of the carbon nanomaterials to the 2,2'-azino-bis(3-ethylbenzothiazoline-6-sulfonic acid) diammonium salt is 1:1, 1:2, 1:3, 1:4 or 2:1.

In one embodiment, the concentration of PBS is between 0.1 M and 0.5 M.

In one embodiment, the pH value of PBS is between pH 4 and pH 9.

In one embodiment, the concentration of the sulfuric acid solution is between 0.1 M and 2 M.

The present disclosure further provides a modified electrode manufactured by the method described above. The surface of the modified electrode comprises 3-ethyl-6-sulfonate benzothiazolinone imine and 3-ethyl-6-sulfonate benzothiazolinone compound.

The present disclosure further provides a use of a modified electrode manufactured by the method described above. The modified electrode is used for protein detection, protein immobilization and related biosensor, electrochemical catalysis or biofuel cells. The protein detection herein is urine albumin detection.

The method of manufacturing a modified electrode of the present disclosure may allow a surface of the modified electrode to have 3-ethyl-6-sulfonate benzothiazolinone imine and 3-ethyl-6-sulfonate benzothiazolone compound, which may make the modified electrode achieve the effect of enhancing the ability of protein adsorption. Moreover, the method of manufacturing the modified electrode of the present disclosure is simple to operate, and the modified electrode may be rapidly prepared within 1 hour. Furthermore, the modified electrode prepared by the method of manufacturing the modified electrode of the present disclosure may be used for protein detection, such as urine albumin detection, protein immobilization and related biosensor, electrochemical catalysis or biofuel cells.

BRIEF DESCRIPTION OF DRAWINGS

In order to explain the technical solutions of the present disclosure more clearly, the following will briefly introduce the drawings used in the description of the embodiments or the related art. Obviously, the drawings described below are only some embodiments of the present disclosure. For those skilled in the art, other drawings can be obtained based on these drawings without making creative efforts. The patent or application file contains at least one drawing executed in color. Copies of this patent or patent application publication with color drawing(s) will be provided by the Office upon request and payment of the necessary fee.

DETAILED DESCRIPTION OF PREFERRED EMBODIMENTS

Figure 1A:
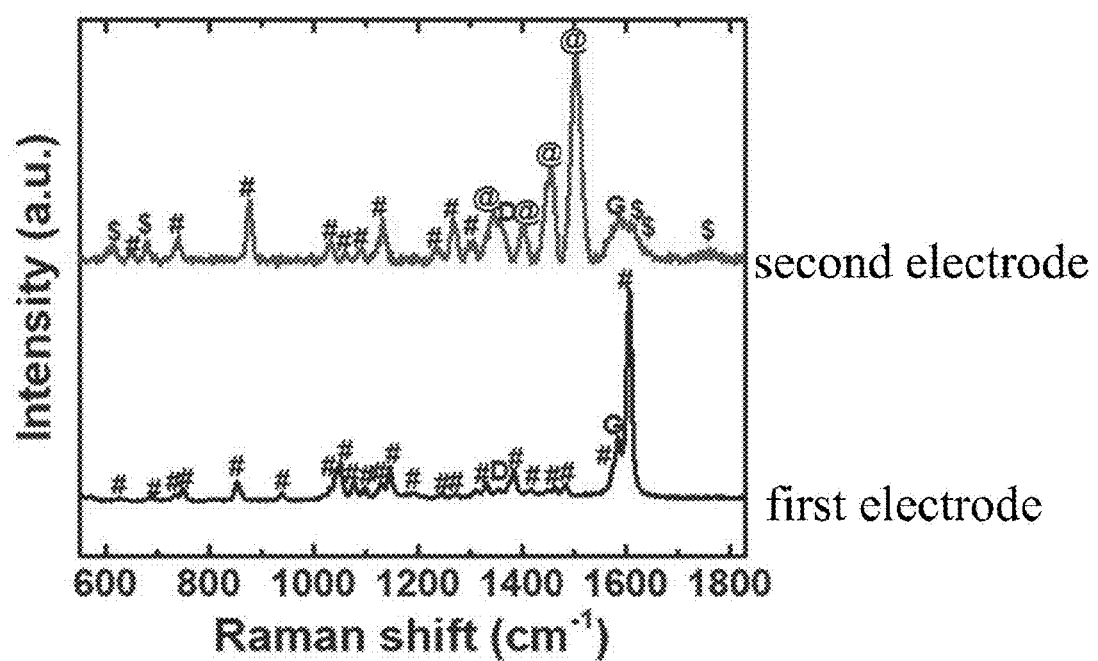
FIG. 1A shows the results of Raman spectra of a first electrode and a second electrode of the present disclosure.

The following describes the embodiment of the present disclosure through specific examples. Those skilled in the field can understand other advantages and effects of the present disclosure from the content disclosed in the present specification. However, the exemplary embodiments disclosed in the present disclosure are merely for illustrative purposes and should not be construed as a limiting the scope of the present disclosure. In other words, the present disclosure can also be implemented or applied by other different specific embodiments, and various details in the present specification can also be modified and changed based on different viewpoints and applications without departing from the concept of the present disclosure.

Unless otherwise described herein, the singular forms "a" and "the" used in the specification and the appended claims of the present disclosure comprise plural entities. Unless otherwise described herein, the term "or" used in the specification and the appended claims of the present disclosure comprises the meaning of "and/or".

Preparation Example 1: Preparation of a First Electrode 30 mg multi-wall carbon nanotubes (MWCNT) and 60 mg 2,2'-azino-bis(3-ethylbenzothiazoline-6-sulfonic acid (ABTS) are added to 10 mL deionized water to form an electrode slurry, and the electrode slurry is subjected to ultrasonic shock for 3 hours to disperse the electrode slurry uniformly. 10 μL electrode slurry is drop-casted on a screen-printed carbon electrode (SPCE) and allowed to be dried to obtain the first electrode (i.e., CNT-ABTS).

Preparation Example 2: Preparation of a Second Electrode

The first electrode obtained in the Preparation Example 1 is placed in 0.1 M PBS (pH 6), and the cyclic voltammetry is performed at a scan rate of 100 mV/s between 0 V and 1.2 V for 75 cycles to obtain an electrochemically pre-treated electrode. The electrochemically pre-treated electrode is rinsed with PBS to obtain a second electrode (i.e., CNT-ABTS$_{CV}$).

Preparation Example 3: Preparation of a Third Electrode 30 mg graphene and 60 mg of 2,2'-azino-bis(3-ethylbenzothiazoline-6-sulfonic acid) diammonium salt are added to 10 mL deionized water to form an electrode slurry, and the electrode slurry is subjected to ultrasonic vibration for 3 hours to disperse the electrode slurry uniformly. 10 μL electrode slurry is drop-casted on a SPCE electrode and allowed to be dried to obtain a graphene electrode. The graphene electrode is placed in a 0.1 M PBS solution (pH 6), and the cyclic voltammetry is performed at a scan rate of 100 mV/s between 0 V and 1.2 V for 75 cycles to obtain an electrochemically pre-treated graphene electrode. The electrochemically pre-treated graphene electrode is rinsed with PBS solution to obtain the third electrode (i.e., graphene-ABTS$_{CV}$).

Preparation Example 4: Preparation of a Fourth Electrode 30 mg graphene oxide (GO) and 60 mg of 2,2'-azino-bis (3-ethylbenzothiazoline-6-sulfonic acid) diammonium salt are added to 10 mL deionized water to form an electrode slurry, and the electrode slurry is subjected to ultrasonic vibration for 3 hours to disperse the electrode slurry uniformly. 10 μL electrode slurry is drop-casted on a SPCE electrode and allowed to be dried to obtain a graphene oxide electrode. The graphene oxide electrode is placed in a 0.1 M PBS solution (pH 6), and the cyclic voltammetry is performed at a scan rate of 100 mV/s between 0 V and 1.2 V for 75 cycles to obtain an electrochemically pre-treated graphene oxide electrode. The electrochemically pre-treated graphene oxide electrode is rinsed with PBS to obtain the fourth electrode (i.e., GO-ABTS$_{CV}$).

Preparation Example 5: Preparation of a Fifth Electrode 30 mg reduced graphene oxide (rGO) and 60 mg of 2,2'-azino-bis(3-ethylbenzothiazoline-6-sulfonic acid) diammonium salt are added to 10 mL deionized water to form an electrode slurry, and the electrode slurry is subjected to ultrasonic vibration for 3 hours to disperse the electrode slurry uniformly. 10 μL electrode slurry is drop-casted on a SPCE electrode and allowed to be dried to obtain a reduced graphene oxide electrode. The reduced graphene oxide electrode is placed in a 0.1 M PBS solution (pH 6), and the cyclic voltammetry is performed at a scan rate of 100 mV/s between 0 V and 1.2 V for 75 cycles to obtain an electrochemically pre-treated reduced graphene oxide electrode. The electrochemically pre-treated reduced graphene oxide electrode is rinsed with PBS solution to obtain the fifth electrode (i.e., rGO-ABTS$_{CV}$).

Preparation Example 6: Preparation of a Fourteenth Electrode

The preparation method of the fourteenth electrode is similar to the preparation method of the Preparation Example 2. The difference is that: the fourteenth electrode is manufactured by the cyclic voltammetry method, which is performed at a scan rate of 100 mV/s between 0 V and 1.2 V for 75 cycles in 0.5 M PBS solution to obtain the fourteenth electrode.

Preparation Example 7: Preparation of a Fifteenth Electrode, a Sixteenth Electrode, a Seventeenth Electrode The preparation methods of the fifteenth electrode, the sixteenth electrode, and the seventeenth electrode are similar to the preparation of the Preparation Example 2. The difference is that: the fifteenth electrode, the sixteenth electrode, and the seventeenth electrode are manufactured by the use of the cyclic voltammetry method for the electrochemical pretreatment, which are performed at a scan rate of 500 mV/s between 0 V and 1.2 V for 75 cycles, 105 cycles, and 225 cycles, respectively, to obtain the fifteenth electrode, the sixteenth electrode, and the seventeenth electrode.

Preparation Example 8: Preparation of an Eighteenth Electrode, a Nineteenth Electrode, and a Twentieth Electrode The preparation methods of the eighteenth electrode, the nineteenth electrode, and the twentieth electrode are similar to the preparation method of the Preparation Example 2. The difference is that: the eighteenth electrode, the nineteenth electrode, and the twentieth electrode are manufactured by using cyclic voltammetry method for the electrochemical pretreatment, which are performed with different potential windows ranging from 0.0 V to 1.0 V vs. Ag/AgCl, ranging from 0.0 V to 1.4 V vs. Ag/AgCl, and ranging from 0.0 V to 1.6 V vs. Ag/AgCl, respectively, to obtain the eighteenth electrode, the nineteenth electrode, and the twentieth electrode.

Preparation Example 9: Preparation of a Twenty-First Electrode, a Twenty-Second Electrode, and a Twenty-Third Electrode The preparation methods of the twenty-first electrode, the twenty-second electrode, and the twenty-third electrode are similar to the preparation method of the Preparation Example 2. The difference is that: the twenty-first electrode, the twenty-second electrode, and the twenty-third electrode are manufactured by performing electrochemical pretreatment using the constant potential method at 1.0 V vs. Ag/AgCl, 1.2 V vs. Ag/AgCl, and 1.4 V vs. Ag/AgCl, respectively, to obtain the twenty-first electrode, the twenty-second electrode, and the twenty-third electrode.

Preparation Example 10: Preparation of a Twenty-Fourth Electrode, A Twenty-Fifth Electrode, a Twenty-Sixth Electrode, and a Twenty-Seventh Electrode The preparation methods of the twenty-fourth electrode, the twenty-fifth electrode, the twenty-sixth electrode, and the twenty-seventh electrode are similar to the preparation method of Preparation Example 2. The difference is that: the twenty-fourth electrode, the twenty-fifth electrode, the twenty-sixth electrode, and the twenty-seventh electrode are manufactured by performing electrochemical pretreatment using the constant current density method with a total charge of 46.0 mC cm$^{-2}$ at applied current densities of 0.5 mA cm$^{-2}$, 1.0 mA cm$^{-2}$, 2.0 mA cm$^{-2}$, and 5.0 mA cm$^{-2}$, respectively, to obtain the twenty-fourth electrode, the twenty-fifth electrode, the twenty-sixth electrode, and the twenty-seventh electrode.

Example 1: Analysis on the Physical Property of the First Electrode and the Second Electrode The physical property of the first electrode and the second electrode are analyzed by Raman spectrometer (purchased from Thermo Fisher, model: DXR) with a laser light wavelength of 532 nm. The analyses of the Raman Spectra are performed by the software of KnowItAll® Informatics System. The results are shown in FIG. 1A and Table 1. Table 1 shows the vibration modes represented by each characteristic peak. The results show that the Raman spectrum of the first electrode presents strong characteristic peaks at 1605 cm$^{-1}$ and 1574 cm$^{-1}$; ABTS characteristic peaks appear at 1484 cm$^{-1}$, 1383 cm$^{-1}$, 1345 cm$^{-1}$, 1145 cm$^{-1}$, 1129 cm$^{-1}$, 1051 cm$^{-1}$, and 852 cm$^{-1}$, and G peak (G band) signal and D peak (D band) signal appear at 1584 cm$^{-1}$ and 1354 cm$^{-1}$, respectively, indicating that CNT-ABTS is indeed present on the first electrode.

The characteristic peaks of the Raman spectrum of the second electrode at 1646 cm$^{-1}$ and 679 cm$^{-1}$ belong to the vibrations of ν (C=N) and δ (NH), respectively, and the characteristic peak at 1637 cm$^{-1}$ belongs to the vibrations of δ (NH) and ν (C=N). It is inferred that a degradation product of 3-ethyl-6-sulfonate benzothiazolinone imine, which has an imine group (C=NH), is generated on the second electrode. In addition, the characteristic peaks at 1760 cm$^{-1}$, 1637 cm$^{-1}$, and 612 cm$^{-1}$ belong to the vibrations of v (C=O, pentacyclic ring), v (C=O, tertiary amine), and δ (NCO), respectively. It is inferred that a degradation product of 3-ethyl-6-sulfonate benzothiazolone, which has a carbonyl group (C=O), is generated on the second electrode.

TABLE 1

Band assignment of Raman Spectra of the first electrode and the second electrode.

Raman shift (cm$^{-1}$)$^a$

| first electrode | second electrode | Assignment$^b$ |
|---|---|---|
| — | 1760 vw, br | v(C=O, ring) |
| — | 1646 w, sh | v(C=NH) |
| — | 1637 w, sh | v(C=O, tertiary amide); δ(NH); v(C=N) |
| 1605 vs | 1609 m, br | v(C=C)BM; vas(S—C=N) |
| 1584 s, br | 1586 m, br | Crystalline graphite (G band) |
| 1574 w/m, sh | 1574 w/m, sh | v(C=C)BM; vs(N—C=N) |
| — | 1505 vs | v(CC)BM |
| 1484 w | — | δ(CH3); v(C=CBM) |
| 1462 vw | 1453 s | δ(CH2); δ(CH3) |
| — | 1444 w/m, sh | γ(CH3); v(CH3); v(CC)BM |
| 1415 vw | — | v(CN); δ(CH2); δ(CH2)BM |
| — | 1404 w/m | v(N=N) |
| — | 1397 w/m | vas(SO2) |
| 1383 w/m | — | vas(NCC) |
| 1354 vw | 1354 m | v(CC); v(CS); crystalline graphite (D band) |
| 1345 vs | 1345 m | vas(SO2) |
| 1330 w | — | v(CC) |
| 1309 vw | 1300 w | v(CN) |
| 1270 vw | 1268 m | v(CN) |
| 1245 vw | 1236 w | vs(SO2) |
| 1145 m | — | v(CC) |
| 1129 w/m | 1132 m | vs(SO2); vas(CN) |
| 1098 w | 1093 vw | v(CN); vs(SO3—H) |
| 1077 w | — | ρ(CH3); δ(CH); v(CSC) |
| 1051 m | — | v(CH)BM |
| 1043 m, sh | — | ρ(CH3); ρ(CH2) |
| 1030 vw, sh | 1032 w | δ(CH3); v(CN) |
| 937 vw | — | ρ(CH3); δ(CH)BM |
| — | 876 m | vs(CN); γ(CH) |
| 852 w | — | v(CH)BM |
| 749 vw | — | vs(CS)TM; δ(CH)BM |
| 734 vw | 740 w | v(S—C); vas(CNC) |
| 689 vw | — | γ(CSC)TM |
| — | 679 w | v(S—C); δ(NH) |
| — | 650 vw | v(C—S—C) |
| 625 vw | — | δ(NCS)TM |
| — | 612 w | v(S—C); δ(NCO) |

$^a$vw: very weak; w: weak; m: medium; s: strong; vs: very strong; sh: shoulder; br: broad;
$^b$v: stretching; δ: in-plane bending; γ: out-of-plane bending; ρ: rocking; s: symmetric; as: antisymmetric; BM: benzene moiety; TM: thiazole moiety.

Figure 1B:
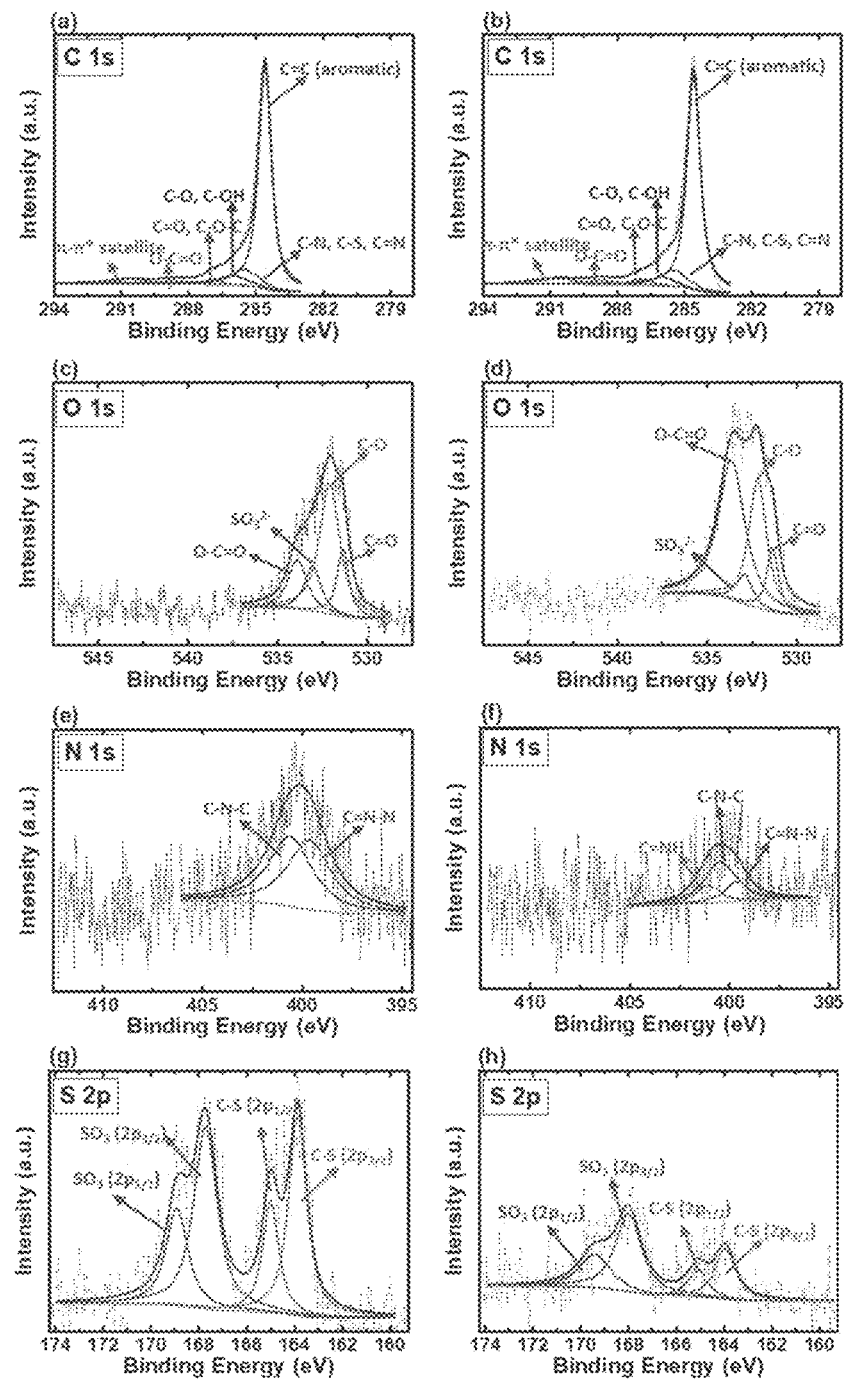
FIG. 1B shows the results of X-ray photoelectron spectrum of the first electrode and the second electrode of the present disclosure. (a), (c), (e) and (g) are the results of carbon spectrum, oxygen spectrum, nitrogen spectrum, and sulfur spectrum of the first electrode, respectively, and (b), (d), (f) and (h) are the results of carbon spectrum, oxygen spectrum, nitrogen spectrum, and sulfur spectrum of the second electrode, respectively.

The surface of the first electrode and the second electrode are irradiated with an aluminum anode target of an X-ray photoelectron spectrometer (purchased from Thermo Scientific, model: Theta Probe), and then the X-ray photoelectron spectra of the first electrode and the second electrode are analyzed by XPSPEAK41 software and are calibrated with C 1 s orbital peak at 284.6 eV to analyze elements and chemical functional groups on the surface of the first and the second electrode. As shown in FIG. 1B, the results show that ABTS is present on the first electrode. In addition, contents of HOC=O functional group and C=O functional group on the second electrode are significantly increased as compared with the first electrode, which indicates that oxidized carbon nanotubes are present on the second electrode after the electrochemical pretreatment. Moreover, contents of C—N—C functional group and C=N—N functional group on the second electrode decrease, and C=NH functional group derived from the degradation product of 3-ethyl-6-sulfonate benzothiazolinone imine are present on the second electrode.

From the above, through the electrochemical pretreatment, the ABTS on the first electrode may be cleaved to form the degradation products, including 3-ethyl-6-sulfonate benzothiazolinone imine and 3-ethyl-6-sulfonate benzothiazolone, and then the surface of the first electrode may be functionalized with the increase of functional groups such as imine groups and carbonyl groups that may interact with proteins (such as hydrogen bonds).

Figure 2A:
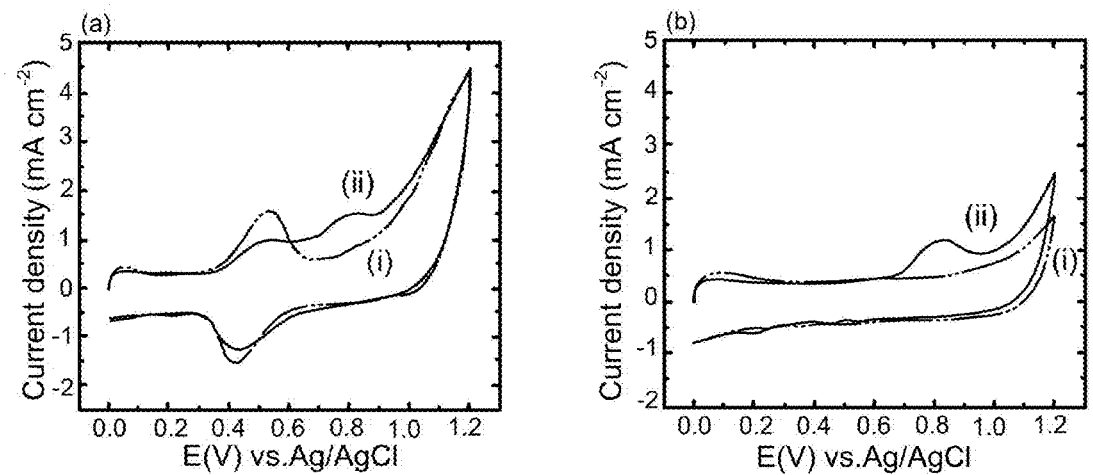
FIG. 2A shows the results of the cyclic voltammetry of the first electrode (a) and the second electrode (b) of the present disclosure. (i) indicates the measurement results of the first electrode and the second electrode after being incubated in the blank PBS solution (0.1 M, pH 6) for 30 minutes, and (ii) indicates the measurement results of the first electrode and second electrode after being incubated in the PBS solution (0.1 M, pH 6) containing 200 ppm human serum albumin (HSA) for 30 minutes.

Example 2. Analysis on Sensing Performance of the First Electrode, the Second Electrode, the Third Electrode, the Fourth Electrode, and the Fifth Electrode Towards the Detection of HSA The first electrode and the second electrode are incubated in a blank PBS (0.1 M, pH 6) and a PBS solution (0.1 M, pH 6) containing 200 ppm HSA for 30 minutes, respectively. After washing the first electrode and the second electrode, the cyclic voltammetry method is performed in the blank PBS solution (0.1 M, pH 6) for one cycle. As shown in FIG. 2A (a) and (b), the current response of the first electrode to the HSA oxidation reaction at a potential of 0.83 V vs. Ag/AgCl is about 0.55 mA cm$^{-2}$, while the current response of the second electrode to the HSA oxidation reaction at a potential of 0.83 V vs. Ag/AgCl is 0.74 mA cm$^{-2}$. It shows that the functionalization of the second electrode through the electrochemical pretreatment may enhance the adsorption capacity and the sensing sensitivity of the second electrode towards the detection of HSA.

Figure 2B:
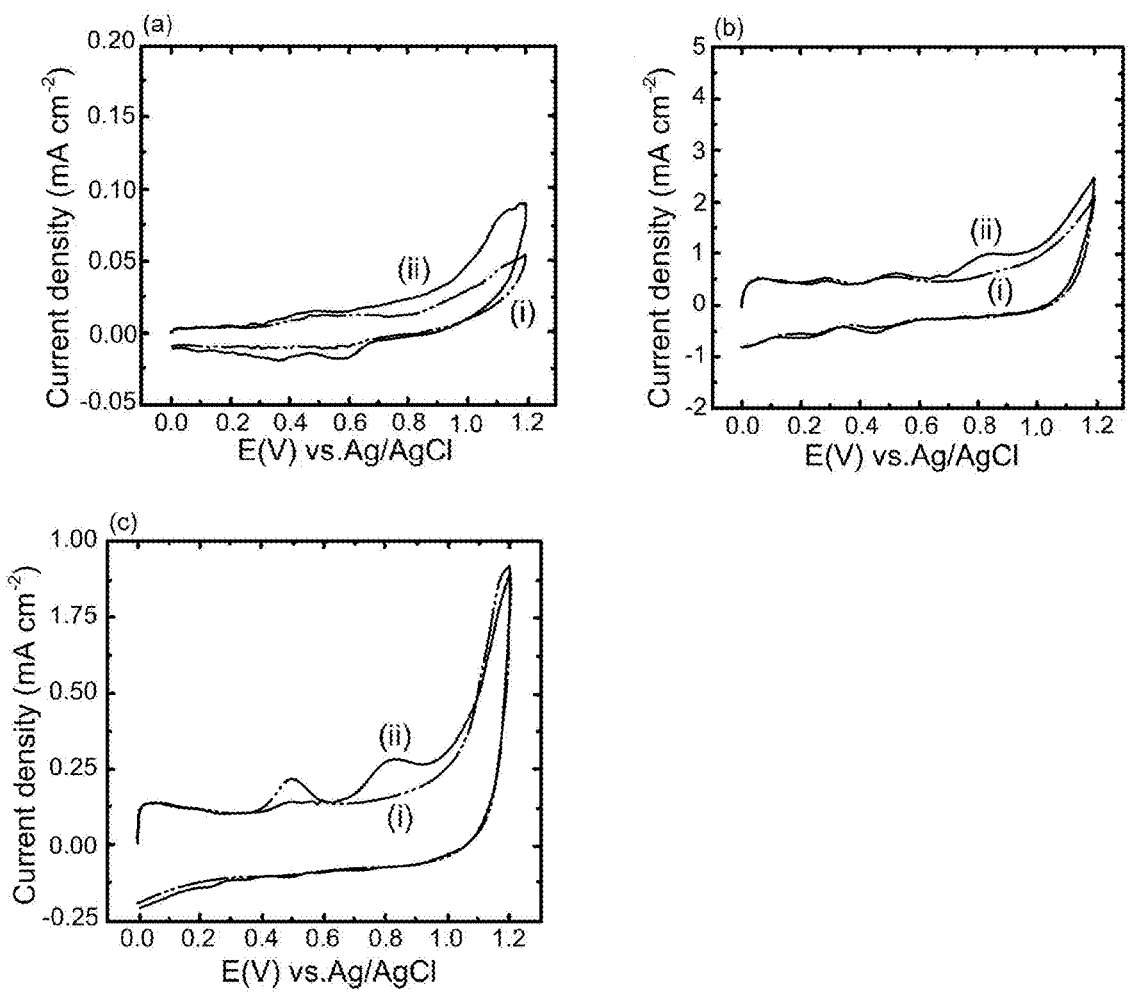
FIG. 2B shows the results of the cyclic voltammetry of the third electrode (a), the fourth electrode (b), and the fifth electrode (c) of the present disclosure. (i) indicates the measurement results of the third electrode, the fourth electrode, and the fifth electrode after being incubated in the blank PBS solution (0.1 M, pH 6) for 30 minutes, and (ii) indicates the measurement results of the third electrode, the fourth electrode, and the fifth electrode after being incubated in the PBS solution (0.1 M, pH 6) containing 200 ppm HSA for 30 minutes.

Each of the third electrode, the fourth electrode, and the fifth electrode is incubated in a blank PBS solution (0.1 M, pH 6) and a PBS solution (0.1 M, pH 6) containing 200 ppm HSA for 30 minutes, respectively. After washing the third electrode, the fourth electrode, and the fifth electrode, the cyclic voltammetry method is performed in the PBS solution (0.1 M, pH 6) for one cycle. As shown in FIG. 2B (a) to (c), the obtained third electrode, the fourth electrode, and the fifth electrode also have good current responses to HSA oxidation reaction.

Figure 3:
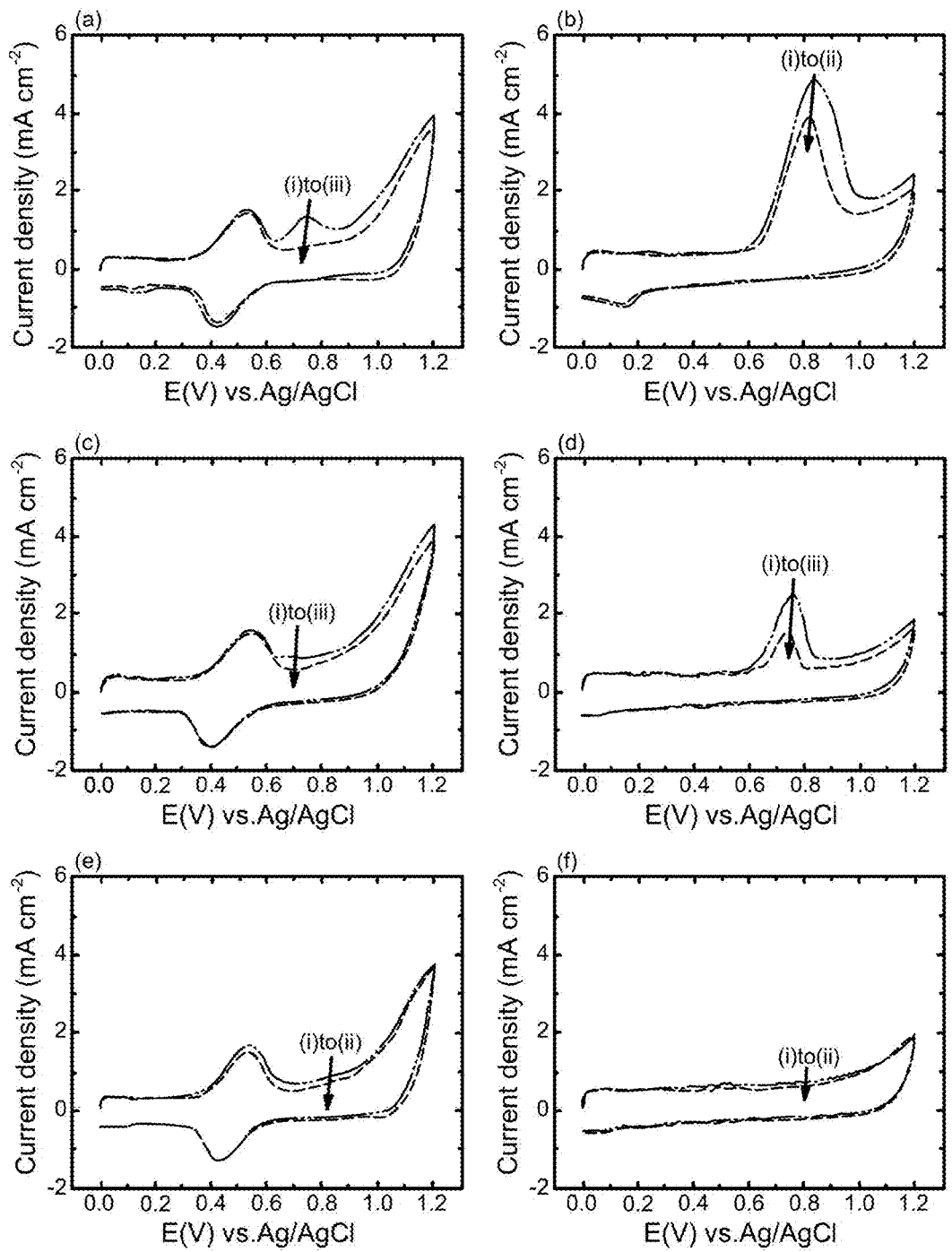
FIG. 3 shows the analysis results of sensing performance of the first electrode and the second electrode of the present disclosure for cysteine, tryptophan, and tyrosine. (a), (c), and (e) indicate the measurement results of cyclic voltammetry of the first electrode in (i) an original solution and (ii) 0.1 M blank PBS solution (pH 6.0) after being incubated in the PBS solution containing 0.35 mM tryptophan (a), 0.35 mM tyrosine (c), and 0.35 mM cysteine (e), respectively for 30 minutes. (b), (d), and (f) indicate the measurement results of cyclic voltammetry of the second electrode in (i) an original solution and (ii) 0.1 M blank PBS solution (pH 6.0) after being incubated in 0.35 mM tryptophan (b), 0.35 mM tyrosine (d), and 0.35 mM cysteine (f), respectively for 30 minutes.

Example 3. Analysis on the Sensing Performance of the First Electrode and the Second Electrode Towards the Detection of Cysteine, Tryptophan, and Tyrosine The first electrode and the second electrode are respectively incubated in a PBS solution (0.1 M, pH 6) and the PBS solutions (0.1 M, pH 6) containing 0.35 mM cysteine, tryptophan, or tyrosine, and then the sensing performance analysis is performed by two methods (i) and (ii). Method (i) is performed by incubating each of the first electrode and the second electrode in the PBS solution (0.1 M, pH 6) containing 0.35 mM cysteine, tryptophan or tyrosine for 30 minutes, respectively, followed by the cyclic voltammetry analysis in-situ applied for one cycle. Method (ii) is performed by incubating each of the first electrode and the second electrode in the PBS solution (0.1 M, pH 6) containing 0.35 mM cysteine, tryptophan or tyrosine for 30 minutes, respectively, followed by the rinsing of the first electrode and the second electrode with the blank PBS solution (0.1 M, pH 6), and cyclic voltammetry analysis in the blank PBS solution (0.1 M, pH 6) for one cycle. As shown in FIG. 3, compared with the first electrode, the second electrode has a strong interaction on both tryptophan and tyrosine, so that tryptophan and tyrosine may be adsorbed on the surface of the second electrode, resulting in the observed current response from the oxidation of tryptophan and tyrosine after the electrode rinsing. The results show that the affinity of the second electrode to amino acids may be regulated after the electrochemical pretreatment.

Figure 4:
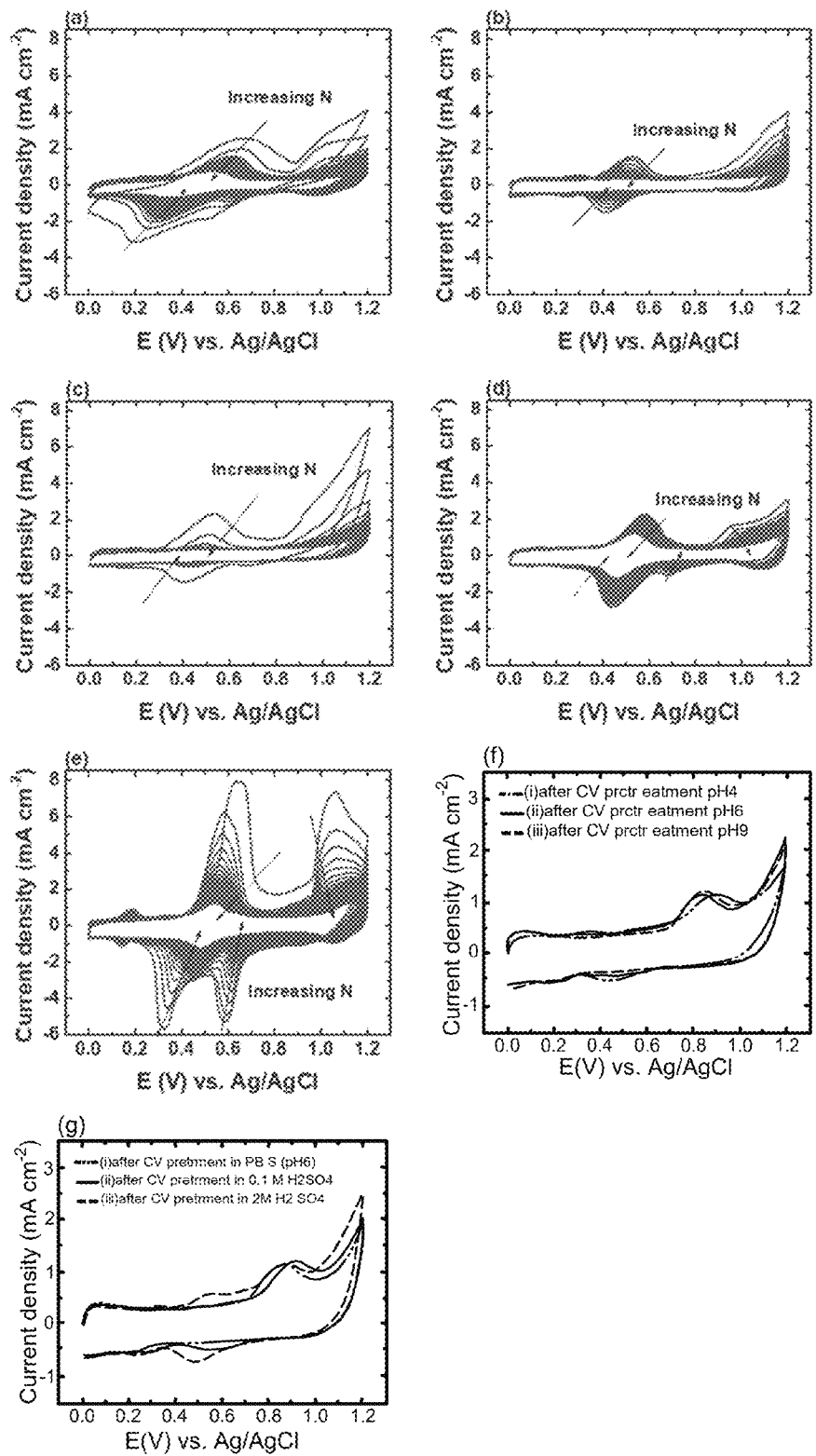
FIG. 4(a)-(e) show the results of the cyclic voltammetry of the first electrode of the present disclosure recorded during the electrochemical pretreatment in different solutions, including (a) 0.1 M PBS (pH 4), (b) 0.1 M PBS (pH 6), (c) 0.1 M PBS (pH 9), (d) 0.1 M sulfuric acid solution ($H_2SO_4$), and (e) 2 M sulfuric acid solution ($H_2SO_4$). (f) shows the cyclic voltammetry of the first electrode in the blank PBS solution (0.1 M, pH 6) after being pretreated in 0.1 M PBS solutions of various pHs, rinsed with blank PBS solution (0.1 M, pH 6.0), and immersed in the PBS solution (0.1 M, pH 6) containing 200 ppm HSA for 30 minutes. (g) shows the cyclic voltammetry of the first electrode in the blank PBS solution (0.1 M, pH 6) after being pretreated in 0.1 M PBS solution (pH 6), 0.1 M $H_2SO_4$, and 2 M $H_2SO_4$, rinsed with blank PBS solution (0.1 M, pH 6.0), and immersed in the PBS solution (0.1 M, pH 6) containing 200 ppm HSA for 30 minutes.

Example 4. Analysis on the Sensing Performance of the First Electrode after Electrochemical Pretreatment Under Different Conditions The first electrode is incubated in 0.1 M PBS solution (pH 4), 0.1 M PBS solution (pH 6), 0.1 M PBS solution (pH 9), 0.1 M $H_2SO_4$, and 2 M $H_2SO_4$, and then the cyclic voltammetry method is performed at a scan rate of 100 mV/s between 0 V and 1.2 V for 75 cycles for electrochemical pretreatment. As shown in FIG. 4(a)-(c), at the end of the electrochemical pretreatment in 0.1 M PBS (pH 4), ABTS/ ABTS+ redox peak may still be observed at 0.4 V vs. Ag/AgCl, presumably caused by the incomplete degradation of ABTS due to the low pH value. As shown in FIG. 4(d)-(e), at the end of the electrochemical pretreatment in 0.1 M $H_2SO_4$ and 2 M $H_2SO_4$, as the pH value of the electrochemical pretreatment environment decreases, it leads to more ABTS residues. The reason for this phenomenon may be that the $ABTS^{2+}$ is relatively stable in the environment of pH<2, resulting in that the $ABTS^{2+}$ may not be completely degraded.

The first electrode is incubated in 0.1 M PBS solution (pH 4), 0.1 M PBS solution (pH 6), 0.1 M PBS solution (pH 9), 0.1 M $H_2SO_4$, and 2 M $H_2SO_4$, and then the cyclic voltammetry method is performed at a scan rate of 100 mV/s between 0 V and 1.2 V for 75 cycles for electrochemical pretreatment. After the electrochemical pretreatment, the obtained electrode is then incubated in the PBS solution (0.1 M, pH 6) containing 200 ppm HSA for 30 minutes, after which the electrode is rinsed and subjected to cyclic voltammetry in blank PBS solution (0.1 M, pH 6) for one cycle to analyze the adsorption of HSA. As shown in FIG. 4(f), (i)-(iii) show the charge resulted from the HSA oxidation are 51.9 μC, 59.3 μC, and 71.2 μC, respectively. As shown in FIG. 4(g), (i)-(iii) show the charge resulted from the HSA oxidation are 77.0 μC, 57.5 μC, and 26.3 μC, respectively. The results show that the charge resulted from the HSA oxidation decreases with the decrease in the pH value of the electrolyte solution used for the electrochemical pretreatment. The reason for this phenomenon may be that when the degradation amount of $ABTS^{2+}$ decreases, the amount of imine group and carbonyl group decreases, thereby reducing the protein adsorption capacity.

From the above, it can be seen that the electrochemical pretreatment should be performed in an environment of pH>4 to achieve a good protein adsorption capacity, and thus sening performance. In addition, the electrochemical pretreatment in the environment of pH 9 requires less cycles for the complete degradation of $ABTS^{2+}$. Therefore, if the electrochemical pretreatment is performed in an environment of pH 9 or the scan rate of cyclic voltammetry is increased, the duration of electrochemical pretreatment may be reduced to less than 15 minutes to rapidly manufacture the electrode.

Example 5. Analysis on the Sensing Performance of the Electrodes Prepared with Various CNT/ABTS Weight Ratios Towards the Detection of HSA The sixth electrode, the seventh electrode, the eighth electrode, and the ninth electrode are manufactured by a method similar to the preparation method of Preparation Example 2 with a weight ratio of CNT:ABTS of 2:1, 1:1, 1:3, and 1:4, respectively. Using the same method as in Preparation Example 2, the sixth electrode, the seventh electrode, the eighth electrode, and the ninth electrode are electrochemically pre-treated in 0.1 M PBS solution (pH 6) to obtain a tenth electrode, an eleventh electrode, a twelfth electrode, and a thirteenth electrode.

A relative content of ABTS on the first electrode, the sixth electrode, the seventh electrode, the eighth electrode, and the ninth electrode may be obtained by comparing the second cycle of the cyclic voltammogram recorded during the electrochemical pretreatment using cyclic voltammetry method in the 0.1 M PBS solution (pH 6). In addition, the second electrode, the tenth electrode, the eleventh electrode, the twelfth electrode, and the thirteenth electrode are incubated in the PBS solution containing 200 ppm HSA for 30 minutes. After washing the second electrode, the tenth electrode, the eleventh electrode, the twelfth electrode, and the thirteenth electrode, the cyclic voltammetry method is performed in the PBS solution (0.1 M, pH 6) for one cycle.

Figure 5:
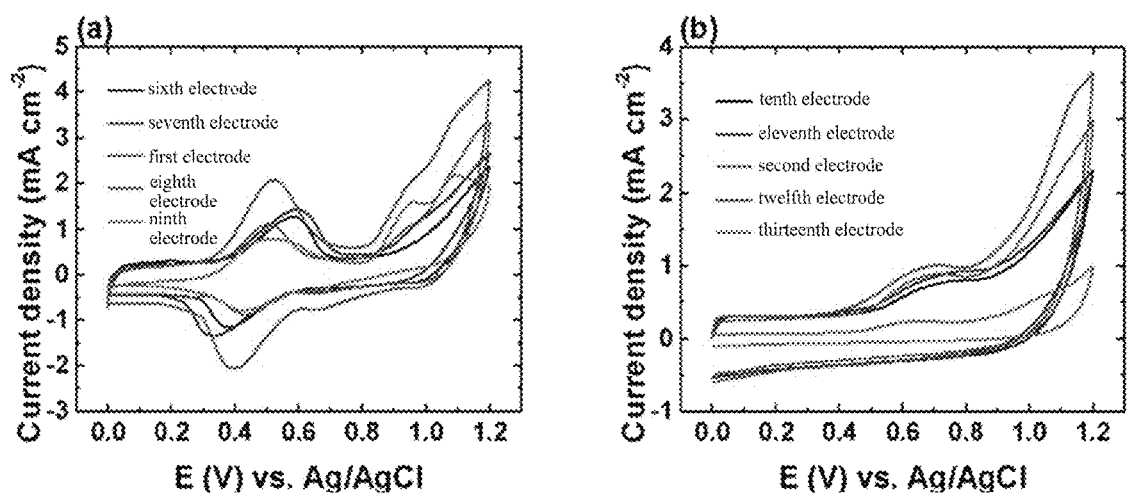
FIG. 5 shows the characterization on the sensing performance of the electrodes of various CNT/ABTS weight ratio manufactured by the present disclosure towards the detection of HSA.

As shown in FIG. 5, the results show that compared with the sixth electrode, the seventh electrode, the eighth electrode, and the ninth electrode, the first electrode prepared with the CNT:ABTS weight ratio of 1:2 has the largest ABTS oxidation peak area at 0.5 V vs. Ag/AgCl, which indicates that the first electrode may have the highest loading amount of ABTS. Therefore, the first electrode may generate more $ABTS^{2+}$ degradation products and be functionalized to adsorb HSA during the electrochemical pretreatment process, so that the second electrode has better sensitivity and adsorption capacity for HSA oxidation and adsorption.

Figure 6:
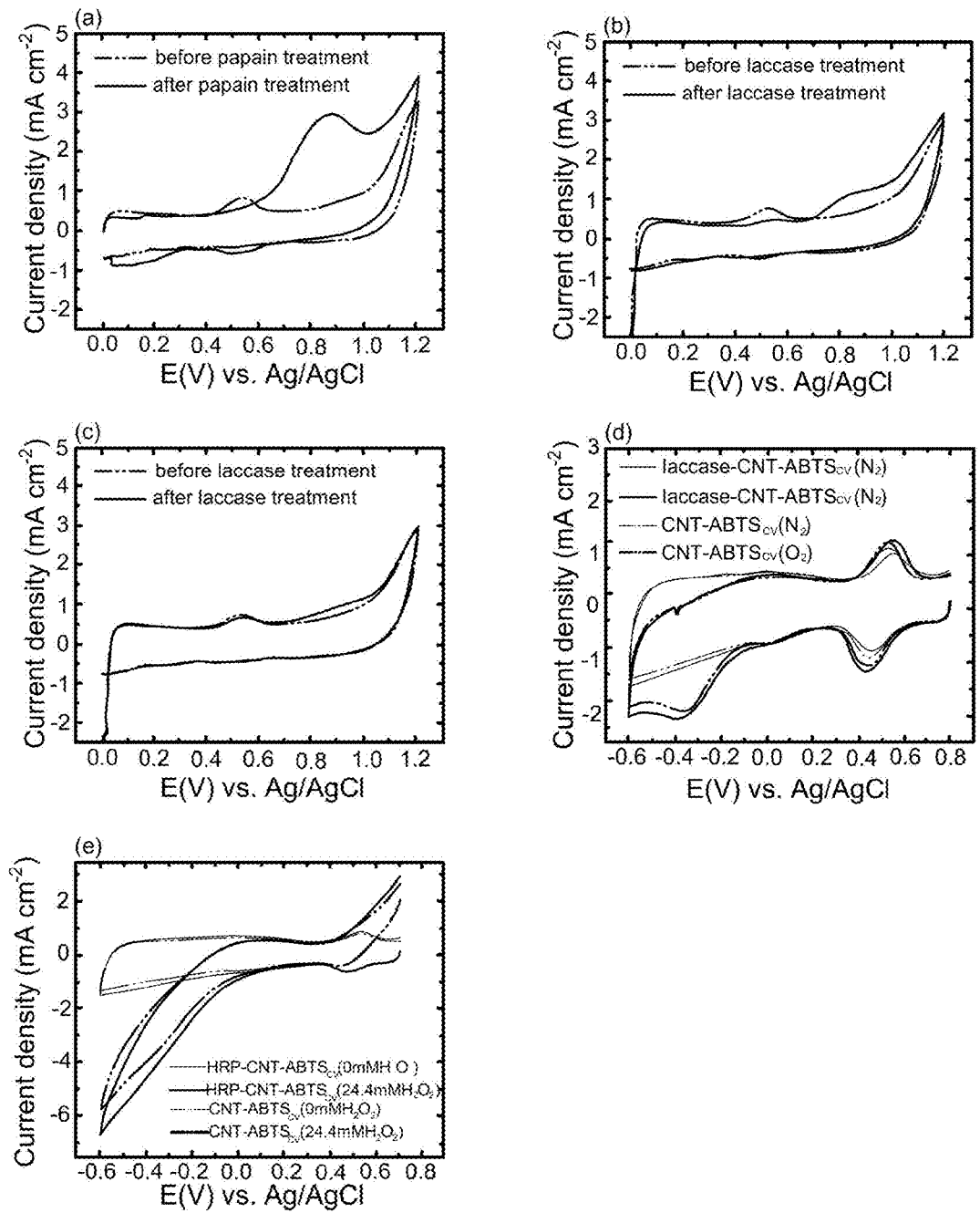
FIG. 6(a)-(c) show cyclic voltammetry of the second electrode of the present disclosure before and after enzyme immobilization. (d)-(e) show the analysis results of the catalytic activity of the second electrode of the present disclosure before and after enzyme immobilization.

Example 6. Enzyme Immobilization of the Second Electrode and Characterization on the Enzymatic Activity of the Second Electrode The second electrode is incubated in an acetate buffer solution containing 5000 ppm papain, 2000 ppm laccase, and 20 ppm horseradish peroxidase (HRP) or in the acetate buffer without enzymes. The cyclic voltammetry method is performed in the PBS (0.1 M, pH 6) for one cycle. FIG. 6(a)-(c) show that a clear oxidation peak appears at E=0.7 V to 1.0 V vs. Ag/AgCl, which is caused by electrochemical oxidation of tyrosine or tryptophan present in the subunits of the enzymes. This result suggests that papain, laccase, and HRP have been successfully immobilized on the second electrode. FIG. 6(d) shows that the electrocatalytic activity of the laccase modified second electrode is higher than that of the pristine second electrode. FIG. 6(e) reveals that the HRP-modified second electrode exhibited higher catalytic current for the reduction of hydrogen peroxide than the pristine second electrode. From the above experiments, it can be seen that the laccase and horseradish peroxidase immobilized on the second electrode still have electrocatalytic activity, which may be applied to electrocatalytic oxygen reduction reaction or hydrogen peroxide reduction reaction in biofuel cells.

Example 7. Analysis of the Sensing Performance of the Fourteenth Electrode

Figure 7:
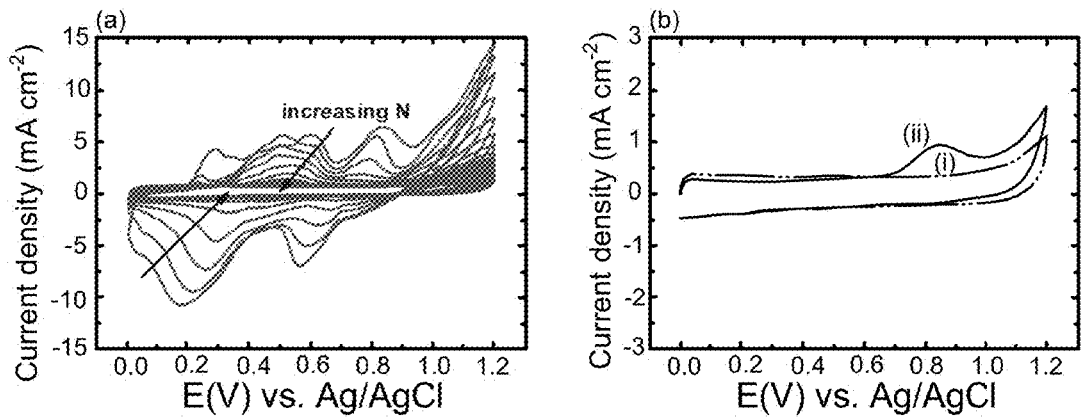
FIG. 7(a) shows the cyclic voltammetry of the first electrode of the present disclosure recorded during the pretreatment in PBS (0.5 M, pH 6). The electrode obtained after this pretreatment is designated as the fourteenth electrode of the present disclosure. (b)-(i) indicates the measurement result of the fourteenth electrode after being incubated in the blank PBS solution (0.1 M, pH 6) for 30 minutes, and (b)-(ii) indicates the measurement result of the fourteenth electrode after being incubated in the PBS solution (0.1 M, pH 6) containing 200 ppm HSA for 30 minutes.

The method of analyzing the sensing performance of the fourteenth electrode is similar to the method of analyzing the sensing performance described in Example 2 and Example 4. Please refer to FIG. 7, the result shows that the fourteenth electrode may completely cleave ABTS after cyclic voltammetry treatment in 0.5 M PBS solution (pH 6). In addition, after performing the cyclic voltammetry in 0.5 M PBS solution (pH 6), the performance of the fourteenth electrode for HSA adsorption and detection is similar to that of the second electrode.

Figure 8:
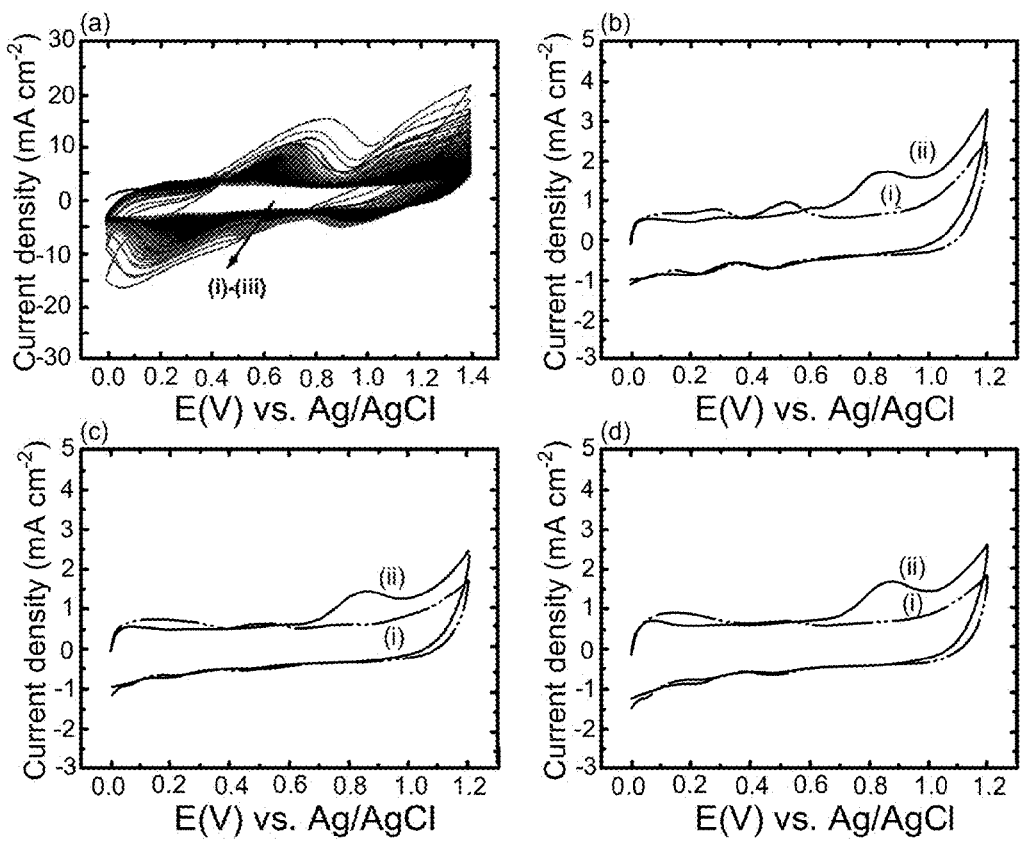
FIG. 8(a) shows the cyclic voltammetry of the first electrode during the electrochemical pretreatment using the cyclic voltammetry method by potential cycling at a scan rate of 500 mV/s between 0 V and 1.2 V vs. Ag/AgCl for (i) 75 cycles (i.e., the fifteenth electrode), (ii) 105 cycles (i.e., the sixteenth electrode), and (iii) 225 cycles (i.e., the seventeenth electrode). (b)-(i) indicates the measurement results of the fifteenth electrode after being incubated in the blank PBS solution (0.1 M, pH 6) for 30 minutes, and (b)-(ii) indicates the measurement results of the fifteenth electrode after being incubated in the PBS solution (0.1 M, pH 6) containing 200 ppm HSA for 30 minutes. (c)-(i) indicates the measurement results of the sixteenth electrode after being incubated in the blank PBS solution (0.1 M, pH 6) for 30 minutes, and (c)-(ii) indicates the measurement results of the sixteenth electrode after being incubated in the PBS solution (0.1 M, pH 6) solution containing 200 ppm HSA for 30 minutes. (d)-(i) indicates the measurement results of the seventeenth electrode after being incubated in the blank PBS solution (0.1 M, pH 6) for 30 minutes, and (d)-(ii) indicates the measurement results of the seventeenth electrode after being incubated in the PBS solution (0.1 M, pH 6) containing 200 ppm HSA for 30 minutes.

Example 8. Analysis on the Sensing Performance of the Fifteenth Electrode, the Sixteenth Electrode, and the Seventeenth Electrode The method of analyzing the sensing performance of the fifteenth electrode, the sixteenth electrode, and the seventeenth electrode is similar to the method of analyzing the sensing performance described in Example 2 and Example 4. Please refer to FIG. 8, the results show that fifteenth electrode, the sixteenth electrode, and the seventeenth electrode may completely cleave ABTS after cyclic voltammetry treatment in 0.1 M PBS solution (pH 6). In addition, after performing the cyclic voltammetry in 0.1 M PBS (pH 6), the performance of the fifteenth electrode, the sixteenth electrode, and the seventeenth electrode for HSA adsorption and detection is similar to that of the second electrode.

Figure 9:
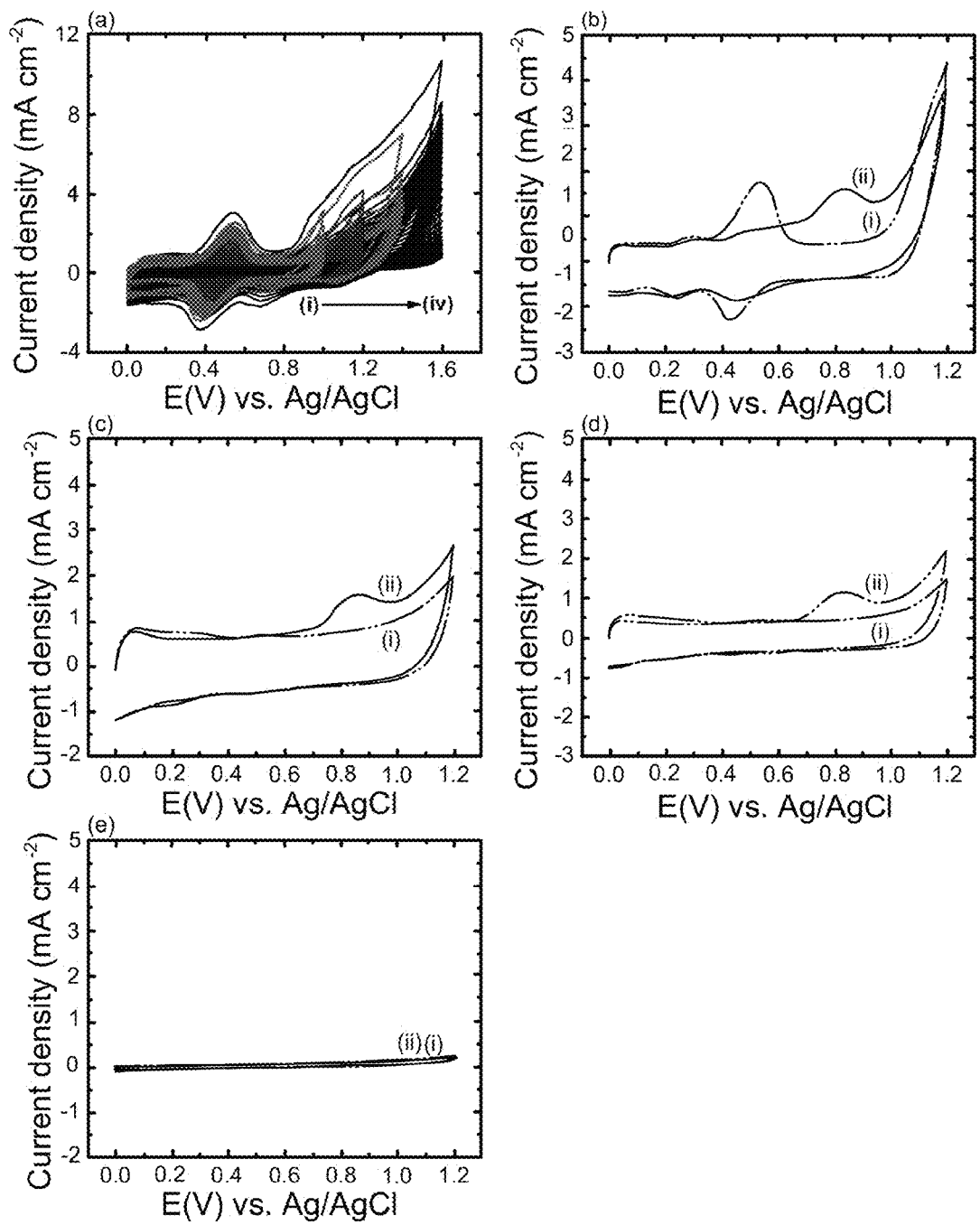
FIG. 9(a) shows the cyclic voltammetry of the first electrode recorded during the electrochemical pretreatment using cyclic voltammetry method with different potential windows (i) ranging from 0.0 V to 1.0 V vs. Ag/AgCl (i.e., the eighteenth electrode), (ii) ranging from 0.0 V to 1.2 V vs. Ag/AgCl (i.e., the second electrode), (iii) ranging from 0.0 V to 1.4 V vs. Ag/AgCl (i.e., the nineteenth electrode), and (iv) ranging from 0.0 V to 1.6 V vs. Ag/AgCl (i.e., the twentieth electrode). (b)-(i) indicates the measurement results of the eighteenth electrode after being incubated in the blank PBS solution (0.1 M, pH 6) for 30 minutes, and (b)-(ii) indicates the measurement results of the eighteenth electrode after being incubated in the PBS solution (0.1 M, pH 6) containing 200 ppm HSA for 30 minutes. (c)-(i) indicates the measurement results of the second electrode after being incubated in the blank PBS solution (0.1 M, pH 6) for 30 minutes, and (c)-(ii) indicates the measurement results of the second electrode after being incubated in the PBS solution containing 200 ppm HSA for 30 minutes. (d)-(i) indicates the measurement results of the nineteenth electrode after being incubated in the blank PBS solution (0.1 M, pH 6) for 30 minutes, and (d)-(ii) indicates the measurement results of the nineteenth electrode after being incubated in the PBS solution (0.1 M, pH 6) containing 200 ppm HSA for 30 minutes. (e)-(i) indicates the measurement results of the twentieth electrode after being incubated in the blank PBS solution (0.1 M, pH 6) for 30 minutes, and (e)-(ii) indicates the measurement results of the twentieth electrode after being incubated in the PBS solution (0.1 M, pH 6) containing 200 ppm HSA for 30 minutes.

Example 9. Analysis of the Sensing Performance of the Eighteenth Electrode, the Second Electrode, the Nineteenth Electrode, and the Twentieth Electrode The method of analyzing the sensing performance of the eighteenth electrode, the second electrode, the nineteenth electrode, and the twentieth electrode is similar to the method of analyzing the sensing performance described in Example 2 and Example 4. Please refer to FIG. 9, the results show that the nineteenth electrode treated with different potential windows may completely cleave ABTS. In addition, the performance of the nineteenth electrode for HSA adsorption and detection is similar to that of the second electrode shown in Example 8. If the potential window of the electrochemical pretreatment is too high, such as the twentieth electrode, the electrode material may be destroyed and the performance of the resultant electrode for HSA adsorption and detection may be impaired.

Figure 10:
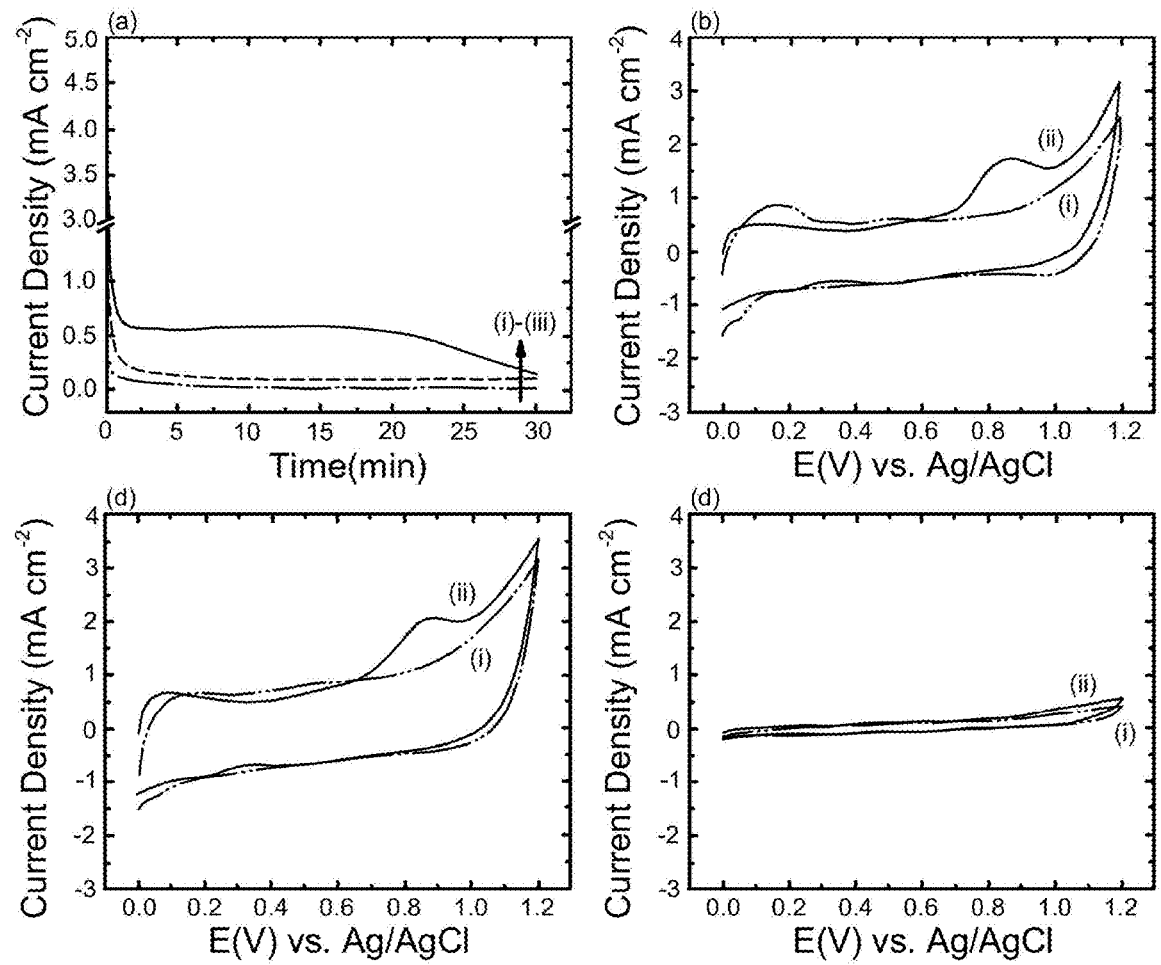
FIG. 10(a) shows the current transients of the first electrode of the present disclosure recorded during the electrochemical pretreatment under at constant applied potentials of (i) 1.0 V vs. Ag/AgCl (i.e., the twenty-first electrode), (ii) 1.2 V vs. Ag/AgCl (i.e., the twenty-second electrode), and (iii) 1.4 V vs. Ag/AgCl (i.e., the twenty-third electrode). (b)-(i) indicates the measurement results of the twenty-first electrode after being incubated in the blank PBS solution (0.1 M, pH 6) for 30 minutes, and (b)-(ii) indicates the measurement results of the twenty-first electrode after being incubated in the PBS solution (0.1 M, pH 6) containing 200 ppm HSA for 30 minutes. (c)-(i) indicates the measurement results of the twenty-second electrode after being incubated in the blank PBS solution (0.1 M, pH 6) for 30 minutes, and (c)-(ii) indicates the measurement results of the twenty-second electrode after being incubated in the PBS solution (0.1 M, pH 6) containing 200 ppm HSA for 30 minutes. (d)-(i) indicates the measurement results of the twenty-third electrode after being incubated in the blank PBS solution (0.1 M, pH 6) for 30 minutes, and (d)-(ii) indicates the measurement results of the twenty-third electrode after being incubated in the PBS solution (0.1 M, pH 6) containing 200 ppm HSA for 30 minutes.

Example 10. Analysis on the Sensing Performance of the Twenty-First Electrode, the Twenty-Second Electrode, and the Twenty-Third Electrode The method of analyzing the sensing performance of the twenty-first electrode, the twenty-second electrode, and the twenty-third electrode is similar to the method of analyzing the sensing performance described in Example 2 and Example 4. Please refer to FIG. 10, the results show that the twenty-first electrode and the twenty-second electrode treated with constant potential may completely cleave ABTS. In addition, the performance of the twenty-first electrode and the twenty-second electrode for HSA adsorption and detection is similar to that of the second electrode shown in Example 8. Electrochemical pretreatment with a higher constant potential, such as the twenty-third electrode, may destroy the electrode material and impair its performance for HSA adsorption and detection.

Figure 11:
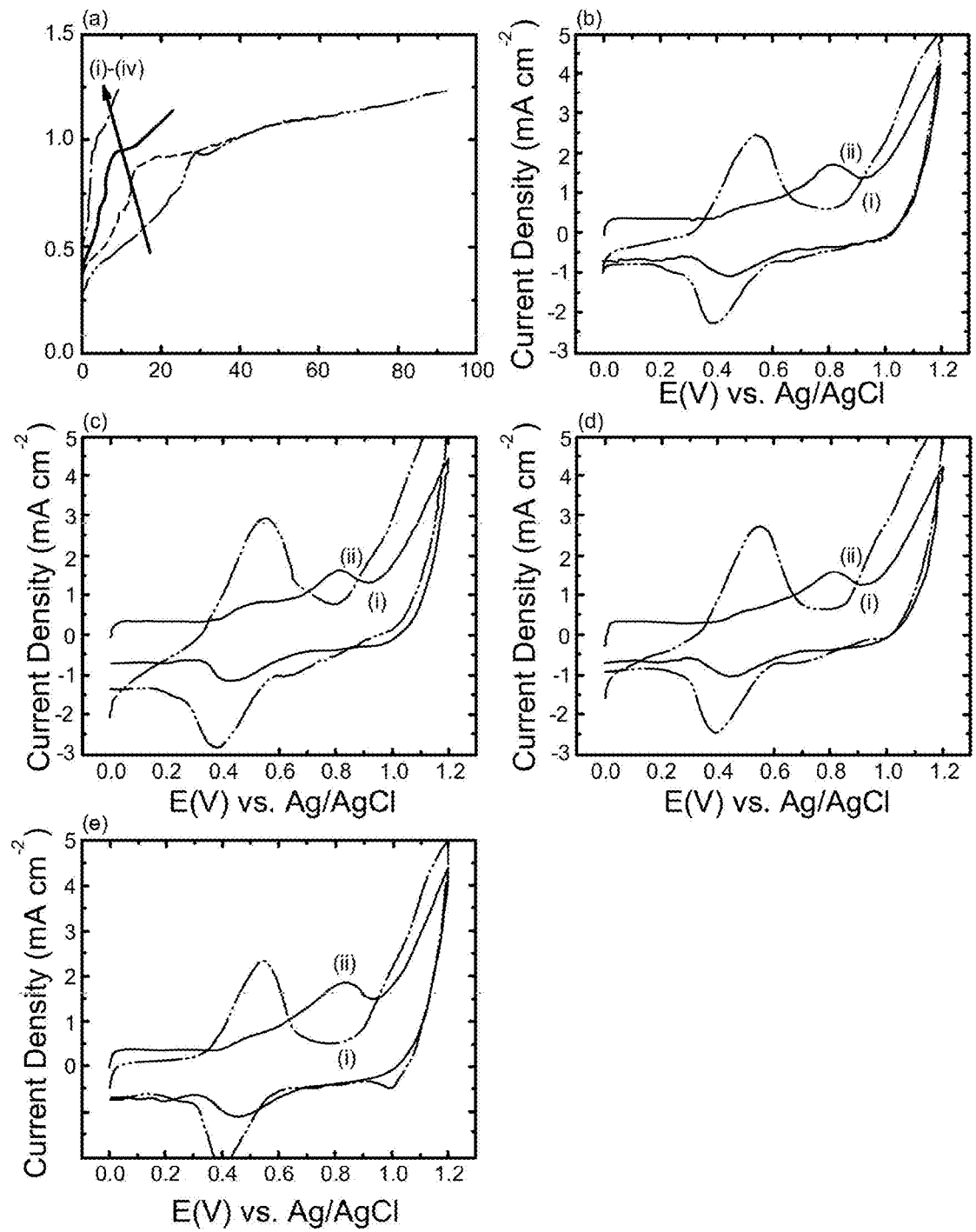
FIG. 11(a) shows the results of the chronopotentiometry of the first electrode of the present disclosure recorded during the electrochemical pretreatment at constant applied current densities of (i) 0.5 mA cm$^{-2}$ (i.e., the twenty-fourth electrode), (ii) 1.0 mA cm$^{-2}$ (i.e., the twenty-fifth electrode), (iii) 2.0 mA cm$^{-2}$ (i.e., the twenty-sixth electrode), and (iv) 5.0 mA cm$^{-2}$ (i.e., the twenty-seventh electrode). (b)-(i) indicates the measurement results of the twenty-fourth electrode after being incubated in the blank PBS solution (0.1 M, pH 6) for 30 minutes, and (b)-(ii) indicates the measurement results of the twenty-fourth electrode after being incubated in the PBS solution (0.1 M, pH 6) containing 200 ppm HSA for 30 minutes. (c)-(i) indicates the measurement results of the twenty-fifth electrode after being incubated in the blank PBS solution (0.1 M, pH 6) for 30 minutes, and (c)-(ii) indicates the measurement results of the twenty-fifth electrode after being incubated in the PBS solution (0.1 M, pH 6) containing 200 ppm HSA for 30 minutes. (d)-(i) indicates the measurement results of the twenty-sixth electrode after being incubated in the blank PBS solution (0.1 M, pH 6) for 30 minutes, and (d)-(ii) indicates the measurement results of the twenty-sixth electrode after being incubated in the PBS solution (0.1 M, pH 6) containing 200 ppm HSA for 30 minutes. (e)-(i) indicates the measurement results of the twenty-seventh electrode after being incubated in the blank PBS solution (0.1 M, pH 6) for 30 minutes, and (e)-(ii) indicates the measurement results of the twenty-seventh electrode after being incubated in the PBS solution (0.1 M, pH 6) containing 200 ppm HSA for 30 minutes.

Example 11. Analysis on the Sensing Performance of the Twenty-Fourth Electrode, the Twenty-Fifth Electrode, the Twenty-Sixth Electrode, and the Twenty-Seventh Electrode The method of analyzing the sensing performance of the twenty-fourth electrode, the twenty-fifth electrode, the twenty-sixth electrode, and the twenty-seventh electrode is similar to the method of analyzing the sensing performance described in Example 2 and Example 4. Please refer to FIG. 11, the results show that the twenty-fourth electrode, twenty-fifth electrode, twenty-sixth electrode, and twenty-seventh electrode treated with constant current may partially cleave ABTS. In addition, the performance of the twenty-fourth electrode, twenty-fifth electrode, twenty-sixth electrode, and twenty-seventh electrode for HSA adsorption and detection is similar to that of the second electrode shown in Example 8.

Based on the results described above, the present disclosure may allow a surface of the modified electrode to have 3-ethyl-6-sulfonate benzothiazolinone imine and 3-ethyl-6-sulfonate benzothiazolone compound, which may make the modified electrode achieve the effect of enhancing the ability of protein adsorption through electrochemical pretreatment of the electrode. In addition, the manufacturing method of the modified electrode of the present disclosure is simple to operate, and the modified electrode may be rapidly manufactured within 1 hour. Furthermore, the modified electrode manufactured by the method of manufacturing the modified electrode of the present disclosure may be used in protein biosensors such as protein immobilization, urine albumin, electrochemical catalysis or biofuel cells.

The above provides a detailed introduction to the implementation of the present disclosure, and specific examples are used herein to describe the principles and implementations of the present disclosure, and the description of the implementations above is merely used to help understand the present disclosure. Moreover, for those skilled in the art, according to a concept of the present disclosure, there will be changed in the specific embodiment and the scope of present disclosure. In summary, the content of the specification should not be construed as a limitation to the present disclosure.

What is claimed is:

1. A method of manufacturing a modified electrode, comprising steps of:
   mixing carbon nanomaterials with 2,2'-azino-bis(3-ethylbenzothiazoline-6-sulfonic acid) diammonium salt to form an electrode slurry, and drop-casting the electrode slurry on a screen-printed carbon electrode to obtain carbon material modified electrodes; and
   placing the carbon material modified electrodes in a phosphate buffer solution or a sulfuric acid solution, and performing an electrochemical pretreatment by cyclic voltammetry method, constant potential method or constant current density method to obtain electrochemically-pretreated electrodes;
   wherein the cyclic voltammetry method is performed by cycling at a scan rate from 100 mV/s to 500 mV/s between 0 V and 1.4 V vs. Ag/AgCl for 75 to 225 cycles, the constant potential method is performed by applying a potential of between 1.0 V and 1.2 V vs. Ag/AgCl for 1800 seconds, and the constant current density method is performed by applying a current density of between 0.5 mA $cm^{-2}$ and 5.0 mA $cm^{-2}$ and a charge passage of 46.0 mC $cm^{-2}$.

2. The method according to claim 1, wherein after the step of performing the electrochemical pretreatment, the method further comprises a step of:
   rinsing the electrochemically-pretreated electrodes with the phosphate buffer solution.

3. The method according to claim 1, wherein the carbon nanomaterials comprise carbon nanotubes, graphene, graphene oxide or reduced graphene oxide.

4. The method according to claim 1, wherein a weight ratio of the carbon nanomaterials to the 2,2'-azino-bis(3-ethylbenzothiazoline-6-sulfonic acid) diammonium salt is between 1:4 and 2:1.

5. The method according to claim 4, wherein the weight ratio of the carbon nanomaterials to the 2,2'-azino-bis(3-ethylbenzothiazoline-6-sulfonic acid) diammonium salt is 1:1, 1:2, 1:3, 1:4 or 2:1.

6. The method according to claim 1, wherein a concentration of the phosphate buffer solution is between 0.1 M and 0.5 M.

7. The method according to claim 1, wherein a pH value of the phosphate buffer solution is between pH 4 and pH 9.

8. The method according to claim 1, wherein a concentration of the sulfuric acid solution is between 0.1 M and 2 M.

\* \* \* \* \*